(12) United States Patent
Han et al.

(10) Patent No.: US 9,393,267 B2
(45) Date of Patent: Jul. 19, 2016

(54) GEL DELIVERY SYSTEM FOR TISSUE REPAIR

(75) Inventors: Bo Han, Temple City, CA (US); Kenrick Kuwahara, Woodland Hills, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/709,238

(22) Filed: Feb. 19, 2010

(65) Prior Publication Data

US 2010/0215715 A1    Aug. 26, 2010

Related U.S. Application Data

(60) Provisional application No. 61/153,965, filed on Feb. 19, 2009.

(51) Int. Cl.
*A01N 63/00* (2006.01)
*A61K 9/22* (2006.01)
*A61K 35/12* (2015.01)

(52) U.S. Cl.
CPC ...................................... *A61K 35/12* (2013.01)

(58) Field of Classification Search
USPC .................. 424/93.1, 492; 435/325
See application file for complete search history.

(56) References Cited

U.S. PATENT DOCUMENTS

| | | | | |
|---|---|---|---|---|
| 5,834,232 A | * | 11/1998 | Bishop et al. | 435/68.1 |
| 2006/0286141 A1 | * | 12/2006 | Campbell | 424/423 |
| 2007/0173821 A1 | * | 7/2007 | Trieu | 606/61 |
| 2007/0185426 A1 | * | 8/2007 | Ambrosio et al. | 602/43 |
| 2007/0299043 A1 | * | 12/2007 | Hunter et al. | 514/171 |
| 2008/0038821 A1 | * | 2/2008 | Tachaboonyakiat et al. | 435/378 |
| 2008/0071385 A1 | * | 3/2008 | Binette et al. | 623/23.72 |
| 2008/0199904 A1 | * | 8/2008 | Suslick et al. | 435/34 |
| 2008/0267902 A1 | * | 10/2008 | Enyart et al. | 424/78.31 |

FOREIGN PATENT DOCUMENTS

WO    WO 91/16009    *    4/1991

OTHER PUBLICATIONS

By Orban (J. of biomedical materials research, Mar. 15, 2004, vol. 68, No. 4, p. 756-762).*
Liora Almany, et al. "Biosynthetic hydrogel scaffolds made from fibrinogen and polyethylene glycol for 3D cell cultures"; Biomaterials (2005): vol. 26 No. 15; pp. 2467-2477.
C.W. Yung, et al. "Transglutaminase crosslinked gelatin as a tissue engineering scaffold", J. Biomed Mater Res. A, (2007): vol. 83 No. 4; pp. 1039-1046.
David J. Mooney, et al. "Cell Delivery Mechanisms for Tissue Repair", Cell Stem Cell (2008): vol. 2 No. 3; pp. 205-213.
Erkki Ruoslahti, "Annu. RGD and other recognition sequences for integrins", Rev. Dell Dev. Biol (1996): vol. 12, pp. 697-715.
Takashi Isobe, et al. Activity-independent cell adhesion to tissue-type transglutaminase is mediated by $\alpha 4 \beta 1$ integrin, European Journal of Cell Biology (1999): vol. 78, No. 12; pp. 876-883.
J.E. Folk, et al. Mechanism and Basis for Specificity of Transglutaminase-catalyzed $\epsilon$-($\gamma$-Glutamyl) Lysine Bond Formation; Adv. Enzymol Related Areas Mol. Bio, (1983): vol. 54, pp. 1-56.
Donald Orlic, et al. "Mobilized bone marrow cells repair the infracted heart, improving function and survival"; Proc Natl. Acad Sci USA, (2001); vol. 98, No. 18, pp. 10344-10349.

* cited by examiner

*Primary Examiner* — Michael C. Wilson
(74) *Attorney, Agent, or Firm* — Ditthavong & Steiner, P.C.

(57) ABSTRACT

The present invention discloses methods and compositions comprising a biocompatible gel that is used in tissue repair and regeneration. Once the gel is administered to a tissue site in need of repair or regeneration, the cells migrate from the gel into the tissue and repair or regenerate the tissue.

12 Claims, 8 Drawing Sheets

2 Days             7 Days

FIGURE 12

GEL DELIVERY SYSTEM FOR TISSUE REPAIR

The present application claims the benefit of the filing date of U.S. Provisional Application No. 61/153,965 filed Feb. 19, 2009, the disclosure of which is incorporated herein by reference in its entirety.

FIELD OF THE INVENTION

The present invention relates in general to tissue repair. More specifically, the invention provides compositions containing a biocompatible hydrogel crosslinked with transglutaminase (Tg) and methods of using the composition to deliver cells to a wound site.

BACKGROUND OF THE INVENTION

Tissue repair has always been one of the goals of tissue engineering. Intense research has been placed on developing methodologies and strategies to regenerate living tissues using synthetic or biological scaffolds. In the past, scaffolds were usually acellular to prevent immune rejection. They were also pre-formed with pores to provide beneficial nutrient exchange and adequate removal of metabolic waste byproducts. To enhance tissue growth and create environments that are favorable for cellular differentiation, these scaffolds were also doused with growth factors or other additives. The growth factor scaffold combination formed a controlled release mechanism as the growth factors diffused from the scaffold as the scaffold degraded or diffused out from its matrix.

Other than growth factors, cells were also delivered to increase aid for repair of the defect site. Surgical procedures and products where autologous cells are extracted, grown in vitro and seeded on a scaffold are increasing in the market. With recent rise in popularity of stem cell regeneration, using cell delivery methods to target the stem cell to the repair site becomes obvious.

Currently, there are two popular methods in cell delivery. One method requires seeding cells on a solid preformed scaffold. The other is to embed the cells in a hydrogel. The hydrogel is an appealing form of biomaterial in that the gels can be injected to its target site through a syringe.

Hoshikawa et al[1] used a styrenated natural polymer gelatin to encapsulate chondrocytes. The gel would crosslink under visible light. Exposure will initiate the cross-linking and the hydrogel is able to gel in situ after injecting through a needle. However, the polymer seems to have low cell viability due to its tightly cross-linked structure.

PEG hydrogel scaffolds [2, 3] are also popular due to PEG's biocompatibility. However its lack of natural component raises questions whether the cells maintain their phenotype or differentiate into their proper form. For example, in Barbetta et al [4], methacrylated derivative of gelatin (a synthetically modified gelatin) seeded with hepatocytes de-differentiated more in comparison to the gelatin cross-linked with transglutaminase. In a later study, the same group mixed in unmodified gelatin with glycosaminoglycan and found it improved the hepatocytes' sustainment of its phenotype [5]. The scaffold was not a hydrogel but proved that having a natural component plays a significant role in the scaffold. Even in a hydrogel, Almany et al [6] combines the synthetic PEG with fibrinogen to compensate for the lack of bioactive signals that are present in the ECM. The study found that without the fibrinogen component the PEG scaffold could not support cell attachment.

Aqueous injectable in situ gelable hydrogels are another type of hydrogel gaining popularity because of their advantages. The hydrogel is able to be injected through a needle and hardens in the surrounding ECM. Weng et al [7] have composed a chitosan and oxidized dextran hydrogel that crosslinks gradually when mixed. Fibroblasts were encapsulated but did not attach well due to the negative charges on the hydrogel or the abundance of COO— groups.

Previous patents have been made concerning encapsulating cells such as U.S. Pat. No. 4,798,786, Jan. 17, 1989, by Thomas R. Tice, and William E. Meyers and U.S. Pat. No. 6,027,744, Feb. 22, 2000 by Charles A. Vacanti and Joseph P. Vacanti. The former discusses methods of encapsulating cells through cross-linked proteins. However, the motive and goal is to keep the cells encapsulated to protect the cells from the immune system and not deliver the cells themselves to the target site. The latter patent uses cell-hydrogel composition to seed a support structure implanted in the body. The cells are delivered in this case but cell survival is dependent on the existence of the support structure.

U.S. Pat. No. 6,699,470 also introduced cell delivery coupled with degradation enzyme under the idea that prolonged cell entrapment can either result in damage and death to cells or hinder the proliferation of cells. However, other papers such as Yung et al [8] and Weng et al. [7] show that the cells survive and can proliferate within the hydrogel entrapment. Using degradation enzyme and inhibitory enzyme to control release can be an option to control release and can easily be done in vitro, but since there are many existing degradative enzymes existing in the body, decreasing the amount of cross-linking within a gel to control release of cells is an easier approach to control release.

U.S. Pat. No. 6,129,761 introduces a hydrogel composition which includes an application for cell delivery. They claim sugar based polymers which are cross-linkable through radical reaction. Several examples of sites are given including mesentery subcutaneous tissue, retropericardium, pro-peritoneal space and intramuscular space. An application for cartilage cell delivery and reconstructive surgery is given. Although hardening the gel and increasing cross-linking is possible, there is no mention of controlled cell delivery.

REFERENCES

1. Hoshikawa, A., et al., *Encapsulation of chondrocytes in photopolymerizable styrenated gelatin for cartilage tissue engineering.* Tissue Eng, 2006. 12(8): p. 2333-41.
2. Rice, M. A. and K. S. Anseth, *Controlling cartilaginous matrix evolution in hydrogels with degradation triggered by exogenous addition of an enzyme.* Tissue Eng, 2007. 13(4): p. 683-91.
3. Dadsetan, M., et al., *Characterization of photo-cross-linked oligo[poly(ethylene glycol)fumarate] hydrogels for cartilage tissue engineering.* Biomacromolecules, 2007. 8(5): p. 1702-9.
4. Barbetta, A., et al., *Enzymatic cross-linking versus radical polymerization in the preparation of gelatin PolyHIPEs and their performance as scaffolds in the culture of hepatocytes.* Biomacromolecules, 2006. 7(11): p. 3059-68.
5. Barbetta, A., et al., *Emulsion templated scaffolds that include gelatin and glycosaminoglycans.* Biomacromolecules, 2008. 9(10): p. 2844-56.
6. Almany, L. and D. Seliktar, *Biosynthetic hydrogel scaffolds made from fibrinogen and polyethylene glycol for 3D cell cultures.* Biomaterials, 2005. 26(15): p. 2467-77.

7. Weng, L., et al., *Non-cytotoxic, in situ gelable hydrogels composed of N-carboxyethyl chitosan and oxidized dextran.* Biomaterials, 2008. 29(29): p. 3905-13.
8. Yung, C. W., et al., *Transglutaminase crosslinked gelatin as a tissue engineering scaffold.* J Biomed Mater Res A, 2007. 83(4): p. 1039-46.

SUMMARY OF THE INVENTION

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

A key technology is the development of an injectable cell delivery system which is biocompatible, biodegradable and adhesive to the wound site. When homogeneously mixed with cells, gel/cell composite can be easy delivered to the lesion site by injection. The gel not only can maintain the carried cells to be viable and proliferative, but also can form in-situ cross-linking between the gel and the wound site extracellular matrices (ECM) to create a strong attachment of gel to the lesion site and localize the delivered cells from diffusion. Cells can be released from the gel by enzymes from cells within the gel or from the surrounding tissues. Encapsulation also shields the cells from the initial immune response of the implanted animal. This cell delivery system may be used in tissue repair and regeneration including, but not limited to bone, cartilage, tendon/ligament, meniscus, skin wound repair, intervertebral disc repair, soft tissue filler, or any tissue comprising cell components collagen. The gels can also be injected into the eye to deliver stem cells to the retina for treating retinal degenerative diseases and stem cells may be locally delivered to spinal cord injuries to enhance healing and recovery of function. The gel can localize the stem cell to target the specific region. As used herein the term "encapsulation" refers to the enclosure of living cells by a gel.

The term "gel" as used herein refers to a jelly-like material. The gel may comprise a gelatin with a percentage that ranges from 4-20% but preferably between 5-10%. The gelatin may be replaced by collagen, fibrin, fibrinogen, albumin, and keratin or other glutamine (Q)/lysine (K) rich peptides. Gels may be in the form of an injectable gel, precast gel, beads, and micelles. More preferably, the gel is in hydrogel form when applied, but solidifies over time. The hydrogel both in liquid and solid form is a biodegradable gel which can be degraded over time by the cells within and the cell from the surrounding environment. More preferably, the gel is a protein based hydrogel with a crosslinking agent that is mixed in with the gel. The hydrogel is transglutaminase reactive with fibrin, fibrinogen, collagen, albumen, involucrin, or gelatin.

Cells encapsulated in hydrogel are viable as they are released into the environment. The encapsulated cells can be used for targeting and repairing tissue damage. The encapsulation also shields the cells from the initial immune response of the implanted animal.

Proteins or peptides may be added to enhance crosslinking and modify physical properties of the gel. Examples include proteins high in glutamine and lysine including but not limited to albumin, gliadins, and caseins and their digested fragments.

Synthetic peptides with single and multiple glutamines and/or lysines can be used to enhance crosslinking. Synthetic peptides sequences with glutamine next to hydrophobic amino acids of F, Y, M, W, L, I, or V are preferred. GVSCKK is an example of a K rich sequence, while KKLQQQLPY is an example of a Q rich sequence. GVSCK-KGGGGGLQQQLPY is an example of a synthetic peptide comprising repeats that may be used as a crosslinking enhancer for gels.

Protein gels can be combined with glycosaminoglycan (GAG) or proteoglycans such as, but no limited to hyluaronic acid, chondroitin sulfate, heparin, and keratan sulfate. Protein gels can also be combined with polysaccharides, such as, but not limited to starch, cellulose, methylcellulose, alginate, agarose, chitin or chitosan, glycogen, xanthan gum, dextran, welan gum, gellan gum, diutan gum, and pullulan. Protein gels can be also combined with fatty substance such as, but not limited to lecithin. Protein gels can be also combined with synthetic polymers such as, but not limited to PEG.

Growth factors specific for the injury repair site can be mixed into the gel to encourage cell differentiation of stem cells within the gel.

Tg concentration can range from 4-250 ug/ml but preferred at 25-100 ug/ml

The present invention is a biologically based cell delivery method. Unlike its synthetic counterparts, the cells are able to affix and proliferate within the gel. When the cells are mixed with the gel, the gel is in the form of liquid like hydrogel.

However with the addition of an enzymatic cross-linker, the gel solidifies without damage to the cells. This invention also incorporates in situ gelation technology, not only to trap gel to the local site, but transglutaminase (Tg) cross-linker also generates bonds between the cell carrier gel and the wound site ECM to create a strong attachment of gel to the lesion site and localize the delivered cells from diffusion. The inventors have also shown that cells are capable of migrating out of the gel toward the repair site.

The technology has being tested extensively with in vitro cell culture systems. It is also applicable to an animal model that mimics rotator cuff injury, and can be used to delivery repairing such as stem cells to the damaged degenerative interverbral disc.

To practice methods of repairing tissue damage, living cells are encapsulated by a protein based hydrogel with a crosslinking agent that is mixed in with the gel. In some embodiments, the encapsulation also shields the cells from the initial immune response of the implanted animal. The encapsulated cells may be tissue precursor cells, stem cells or primary cells extracted from tissue. The precursor cells may be able to differentiate into specific cell types. In some embodiments, the gel is a hydrogel but when applied, solidifies over time. The treated mammal may be a human, mouse, rat, rabbit, cow, pig, horse, goat, sheep, dog, or cat. The gel may further comprise a supply of nutrients for the cells. The crosslinking agent may be transglutaminase, Ca++ dependent transglutaminase, laccase, or tyrosinase. The protein based hydrogel may contain additives that can enhance the crosslinking effect, synthetic and natural peptides containing lysine and glutamine. The method may be used to supplement cells in cell deficient areas or aid in the proliferation of cells.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

Gel Delivery System for Tissue Repair

The invention provides methods of and composition for repairing and growing new tissue by delivering cells through a hydrogel that gels in situ. The hydrogel solidifies in situ creating its own support structure for the cells. As the digestive enzyme is secreted by the encapsulated cells, the cells can migrate out of the gel toward the damaged or repair site. The added cross-linker is required to be non cytotoxic and biocompatible for the survival of the encapsulated cells.

Much research has been performed in the field of acellular synthetic and biological scaffolds which where relies on the surrounding cells to pervade and proliferate onto the material.[2] This technology requires the cells to first identify new scaffold, migrate to the site, and then start the repair process. Cellular delivery technology has shown that cells can take part in the repair of lost damaged and degenerated tissue.[3] Direct injection of cells has shown to be a minimally invasive way to treat damaged tissue.[3, 4] But the scattering of the cells signified a need for targeting or a method of localizing and concentrating the cells. An injectable scaffold with cells seeded onto the matrix may provide improvement where direct injections of cells have failed. A hydrogel like scaffold is a likely solution since it combines advantages of an injection and its localized delivery of cells to the targeted tissue.

Gelatin was chosen as the hydrogel for its biocompatible properties [5]. Gelatin is a denatured form of collagen and formed by a prolonged heating of collagen.[6] Even after the denaturing process, gelatin retains most of the amino acid sequence segments as that of collagen [6, 7]. This retention signifies that most of the integrin binding domains from collagen [8] are available on gelatin. Gelatin also has a less ordered structure similar to heat denatured collagen exposing many of the integrin binding domains for cell attachment, [9] making it a favorable scaffold. However, gelatin's main problem stems from its natural tendency to dissolve at 37° C. To counter this problem, gelatin needs to be crosslinked. Crosslinking can create more intra and intermolecular bonds increasing gelatin melting temperature. It also can retard the protease activity enabling the gelatin to last longer as it biodegrades.[10] Cross-linkers often include synthetic chemicals such as glutaldehyde, formaldehyde, and EDC. These synthetic chemicals have cytotoxic potential and require additional procedures to remove them after the treatment. In situ gelation becomes exceedingly difficult to do since once the cross-linkers are removed, the chemical reaction ends.

Cross-linking is instead performed by an enzymatic cross-linker called transglutaminase. Transglutaminase becomes an advantageous candidate because it is naturally occurring enzyme that is found in almost all living organisms and in variety of tissues [11, 12]. Transglutaminase is also found to play a role as a cell adhesion protein opening possibilities of increasing cell attachment [13, 14]. Its bacterial analogous known as microbial transglutaminase is also known to be innocuous and widely used in food processing for humans consumption [15, 16]. Due to this fact transglutaminase process does not require a wash procedure and can immediately be used after mixing.

Transglutaminase functions by covalently binding the $\epsilon$-amino group of a lysine residue and a $\gamma$-carboxamide group of glutamine.[17] Tranglutaminase can create intramolecular covalent links within gelatin creating a lasting structure that will polymerize when injected. Close proximity and alignment between a glutamine and lysine is the only requirement to promote the crosslinking.[11] Due to the structural amino acid similarities of collagen and gelatin [7], we believed that once injected the gelatin with transglutaminase will form intermolecular links with the collagen of surrounding tissue and once the hydrogel attached itself to the repair site, the cells will be released.

Additional bioactive molecules can be mixed to the hydrogel. Proteins like fibrinogen, small peptide chains containing RGD, or fibronectin can be added to control or increase the cell attachment or proliferation in the gel. Sugar based biopolymers can be added for structural support or prevention of dedifferentiation. Glutamine and lysine containing peptides can also be added to modify mechanical properties of the gel.

Cells can be obtained autologously, from a donor, cell lines or from extracted stem cells. The cells can also be directly used after extraction or after being cultured on tissue culture dishes. The type of cells open to be delivered with this scaffold can be any cells that preferably elicit little or no immune response. Once cells are obtained a mixture of gelatin and tranglutaminase is made and immediately added to the cells. Once the cells have been mixed in, the mixture can be loaded into a syringe. Needle size greater than 30 gauge can be used.

Gel Preparation:

A confluent cell culture plate of stem cells were gently rinsed with PBS solution (8.06 mM sodium phosphate, 1.94 mM potassium phosphate, 2.7 mM KCl and 137 mM NaCl in dH$_2$O at PH7.4) three times to remove the cell medium. After the last rinse of PBS is decanted, a thin layer of 0.25% trypsin in HBSS is added to separate the cells from the plate. The plate is left incubated at 37° C. with $CO_2$ level at 5%. The cells were suspended in 10% FBS/DMEM and aliquoted into $10^6$ cells per tube. The cells were centrifuged and the medium was removed.

The hydrogel solution was made in the 9:1:0.025 ratio mix of 10% gelatin, 10×PBS and tranglutaminase respectively. Stem cells were mixed and suspended in hydrogel solution at concentrations of $10^6$ cells/ml. The hydrogel solution with the cells was loaded into a syringe and injected into the defect site.

Gel/Tg Adherence to the Surrounding Tissue and its Resistance to Pressure:

The transglutaminase also enables the binding of the gelatin to native collagen structures. A burst test was conducted to determine the endurance of the gel/Tg binding to the collagen matrix. Fresh bovine pericardium disc (4 cm diameter) was used in vitro as a collagen matrix and mounted on a water column. A 4 mm diameter hole was punched in the center of the pericardium and filled with 150 ul of freshly mixed gel/Tg. After 30 min of gel curing time, water was added to water column. Pressure (mmHg) was determined by height of water (mm) at which the gel/Tg plug failed divided by the density of mercury (13.6 g/ml).

Gel/Tg sealed defect withstood water pressures at least 2 mins before bursting. Higher concentration of Tg in gel/Tg resisted higher pressure. Gelatin without Tg burst immediately when water pressure increased beyond 2.9 mmHg of pressure. Each sealed defect broke at the interface border between the collagen and the solidified gel. The adhesive bonding strength was determined by the derived formula mentioned in the material methods above and shown in Table 1.

TABLE 1

Calculated adhesive bond strength

| 10% Gelatin mixed with Tg(mg/ml) | Adhesive Bonding Strength ($kN/m^2$) |
|---|---|
| 0.0470 | 318.08 ± 10.13 |
| 0.0235 | 237.03 ± 88.13 |
| 0.0117 | 150.92 ± 75.36 |
| 0 | 14.67 ± 16.94 |

Figure 3:
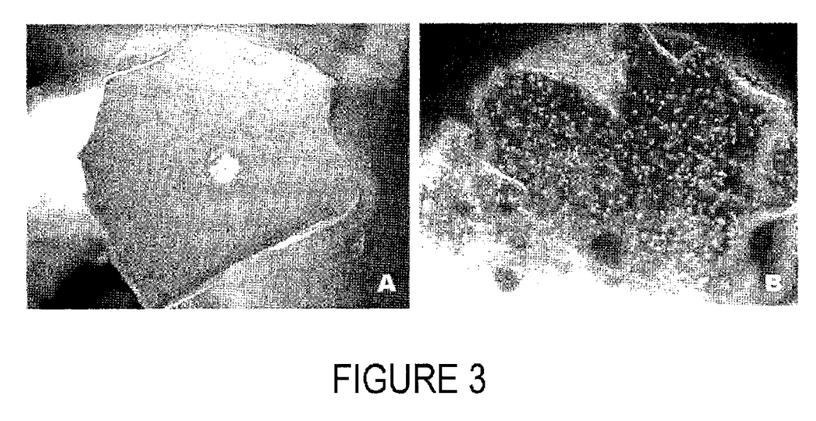
FIG. 3. (A) The hydrogel injected onto a 4 mm diameter defect site made on a bovine pericardium. (B) 40× magnification of the circular defect site. The cells can be seen suspended in the solidified hydrogel.
Figure 4:
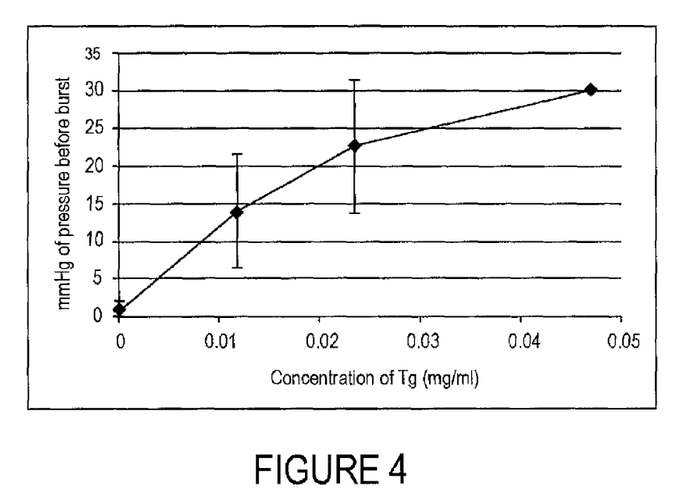
FIG. 4. A burst test was performed by filling 4 mm diameter defect on a bovine pericardium with various concentration of transglutaminase (tg) mixed with gelatin and subjecting it to pressure. The pressure at which the plug at the defect burst was recorded.
Figure 5:
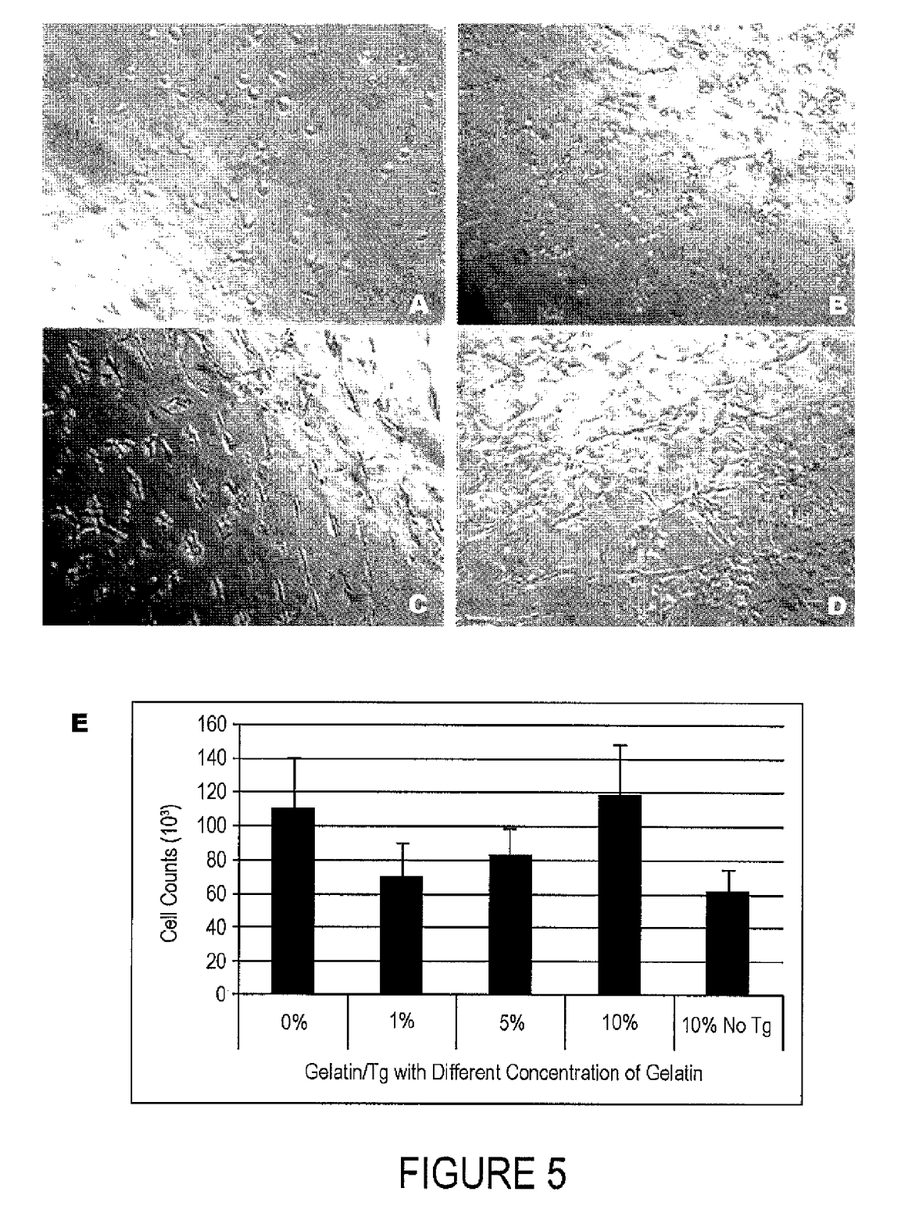
FIG. 5. (A) A 10% gelatin with no transglutaminase. (B) 1% gelatin with Tg. (C) 5% gelatin with Tg. (D) 10% gelatin with Tg. (E) The cell count of MSC after 48 hours on different substrates.

FIG. 4 shows indirectly through the burst test that the binding strength increases between the interface of the gelatin mixture and collagen as transglutaminase concentration is increased. Plain gelatin without any transglutaminase broke quickly. Examples of the defect and the filled gelatin with cells can be viewed on FIG. 3. As the hydrogel is deposited into the target site, the hydrogel solidifies and sticks to the collagenous tissue.

Gelatin itself has adhesive properties and have been considered for use as nontoxic alternative for solvent based glue [28]. But with crosslinked gelatin, adhesiveness can be increased depending on the substrate that is bonded to the gelatin. Chen et al [29] demonstrated the potential of gelatin mixed with transglutaminase as an adhesive to retinal tissue. The study found that lap shear stress of the gelatin-Tg was comparable to other adhesives such as fibrin sealants[30] and chitosan[31] and other various crosslinked gelatin [32]. Although the method used in the previous studies was based on ASTM F2255-03 ("Test Method for Strength Properties of Tissue Adhesives in Lap-Shear by Tension Loading"), this study calculates the adhesion by finding the stress it requires to break at the collagen and gelatin interface. The study confirmed that gel-Tg can adhere to the collagen and the strength increases as the amount of Tg is increased. 0.05 mg/ml of Tg with gelatin was 20 times more adhesive than gelatin by itself. Since the concentration of gelatin is kept constant, the increase is explained by Tg constructing covalent crosslinks between gelatin and collagen. This gives future potential in controlling not only the cell release by the adhesion of the gel/Tg to the surrounding tissue.

In the burst test, gel/Tg-collagen interaction was able to sustain a gradual increase in water pressure as the amount of Tg used was increased. The maximum pressure was held at around 31.3 mmHg comparing to 1.5 mmHg for gelatin without Tg. Hirai et al [33] demonstrated that with collagen gel and smooth muscle cells, they were able to make a tissue engineered vessel that withstood 100 mmHg. Further testing can be discussed where an idea of adding gel/Tg may increase the burst pressure of the vessel since the collagen gel used in that study was not crosslinked.

Optimization of Gel/Tg Delivery

For gel injections, the gel/Tg is required to be in a semi-solidified form to be injected through the syringe without clogging. The gel/Tg in its semi-solidified form is easier to inject and adheres better to the tissue at the repair site than gel/Tg that are completely solidified. Knowing the time frame of gelation from semi-solid to completely solidified aids in the timing of administering the gel. In this study, semi-gelling period is recorded as the time when the liquid gel is able to be injected through a 27 gauge needle. Gel times in minutes are illustrated in Table 2. Concentration below 0.0117 for Tg and below 5% gelatin required time periods that were impractical to be considered for injection during surgery.

TABLE 2

Semi gel time periods for different concentration of gelatin and transglutaminase
Semi Gelling times (mins)

| Gelatin Concentration | Concentration of Transglutaminase | | |
|---|---|---|---|
| | 0.0470 mg/ml | 0.0235 mg/ml | 0.0117 mg/ml |
| 10% gelatin | 10-13 | 20-25 | 30-42 |
| 7.5% gelatin | 13-20 | 30-50 | |
| 5% gelatin | 75-100 | 95-120 | |

EXAMPLE II

Biocompatible Hydrogel for Cell Delivery

Gelatin gel crosslinked with transglutaminase (Tg) as a delivery system for mesenchymal stem cells (MSC) is exemplified. MSCs are isolated and delivered to the repair site by injection. Previous studies have shown the possibility of the gelatin gel crosslinked with transglutaminase to encapsulate cells and be released with trypsin in vitro [10].

However this example demonstrates the injectable cell delivery system by first determining its biocompatibility toward MSC, and then demonstrating the migration of MSC cells from the gel in vitro and in vivo.

Other hydrogels, like the PEG hydrogel scaffolds [20, 21] are used due to PEG's biocompability. However its lack of natural component raises questions about whether the cells maintain its phenotype or differentiate into its proper form. For example, in Barbetta et al [22], a methacrylated derivative of gelatin (a synthetically modified gelatin) seeded with hepatocytes dedifferentiated more in comparison to the gelatin crosslinked with transglutaminase. In a later study, the same group mixed in unmodified gelatin with glycoaminoglycan and found it improved the hepatocytes sustainment of its phenotype.[23] The scaffold was not a hydrogel but proved that having a natural component plays a significant role in the scaffold. Even in a hydrogel, Almany et al [24] combines the synthetic PEG with fibrinogen to compensate for the lack of bioactive signals that are present in the ECM. An Almany et al. [24] study also found that without the fibrinogen component the PEG scaffold could not support cell attachment. Weng et al [25] have composed a chitosan and oxidized dextran hydrogel that crosslinks gradually when mixed. Fibroblasts were encapsulated but did not attach well due to the negative charges on the hydrogel or the abundance of COO— groups. By viewing the proliferation and attachment, gel/Tg may deploy as a temporary platform as cell migrates, proliferates and attaches to the gel, a property that the other hydrogel may lack.

Bone Marrow Stromal Cell Maintenance

Rat bone marrow stromal cells (MSC) were cultured in Dulbecco Modified Eagle's media (Mediatech) supplemented with 10% FBS (Mediatech) and 1% antibiotic/antimyotic solution (Mediatech) in 100 mm tissue culture plate (BD). Cells were passed with a 1:10 split ratio for every two days usually at 70-90% confluence.

Gelatin/Tg Gel Preparation

Microbial Transglutaminase (Tg) from *Streptomyces mobaraense* was obtained from Ajinomoto and further purified with SP Sepharose fast flow column [18]. To prepare the crosslinked gel, Tg concentration was 25 ug/ml in 10% gelatin (bovine skin of 225 bloom, Sigma). Gel mixture was incubated at 37° C. for 1 hour before in vitro and in vivo studies.

Cytotoxicity on Gel/Tg Film

Cells were directly overlaid on gel/Tg was used to test cell proliferation and attachment. In each 24 well plate, 200 μl/well of gel/Tg gel was loaded and air dried. After rinsing with PBS twice, 50 k/well of rat bone marrow stromal cells (MSC) [2] were seeded in 1 ml of 10% FBS/DMEM (Mediatech). The cell number was counted following trypsin detachment at 72 hours. Cell attachment and migration was observed on a daily basis.

In Vitro Cell Delivery

Gel composed of 10% gelatin, 10×PBS, and Tg in a ratio of 9:1:0.025 was gently mixed with $1\times10^6$/ml of MSC cells and 40 μl of the mixture was injected (23 G needle) into each well of a 96 well plate. The gelation time was recorded. After 30 min, 200 μl of 10% FBS/DMEM (Mediatech) was added to cover the gel and the medium was changed every 2-3 days. Cell viability was tested after 3 days by trypan blue staining and cell morphology was monitored up to 10 days. Cell migration from the gel was measured and recorded. The gels with cells migrating out of gels were stained with quick fix (2 min fix, 5 min red 5 min purple.)

In Vivo Cell Delivery

Four male 6 week old Fisher 344 rats (wt 190-210 g) were used for the experiment according to an approved protocol by IACUC, University of Southern California. Prior to surgery, the rats were anesthetized with ketamin/xylazine (10:1 w/w). The area of surgery was shaved and disinfected with iodine and ethanol. A 1-cm incision was made above the shoulder. A portion of the deltoid was detached from the acromion to expose the infraspinatus tendon. Measuring about 5 mm from the humeral insertion of the tendon, a full-thickness defect across 50% of the total width of the infraspinatus tendon was made. 200 ul gelatin-TGase cocktail mixed with $10^6$ cells/ml of GFP labeled MSC was injected through a 23 gauge needle on to the defect site. The injection site was identified with a small suture knot. For closure, deltoid muscle was sutured and the skin was subsequently sutured. No activity restrictions were imposed following surgery.

The injected gels and surrounding tissue were harvested at two days and seven days post-surgery and fixed in 10% formalin neutral buffer solution (pH 7.4), dehydrated in a graded ethanol series, embedded in paraffin and sectioned at 5 um thick with a microtome (Reichert Jung Histocut 820), Fluorescent micrographs were taken from deparaffinized sections with a fluorescent microscope (Leica DM-LB2). The serial sections from the same paraffin blocks were also stained with hemotoxylin and eosin to visualize the cells and extracellular matrix.

Results

Cytotoxicity and Cell Attachment

Gel/Tg was not cytotoxic to the cell when tested with direct overlay models. After 48 hrs from seeding, the cell numbers between the gel/Tg coated surface and the plastic surface had no significant difference. MSC attached and proliferated equally well on gel/Tg coated section of the plate and plastic surface (48 hours). Differences in morphology are observed for different concentration of gelatin. Significant difference is observed ($p<0.05$) between 10% gelatin with Tg and without Tg.

Cell Migration

Figure 1:
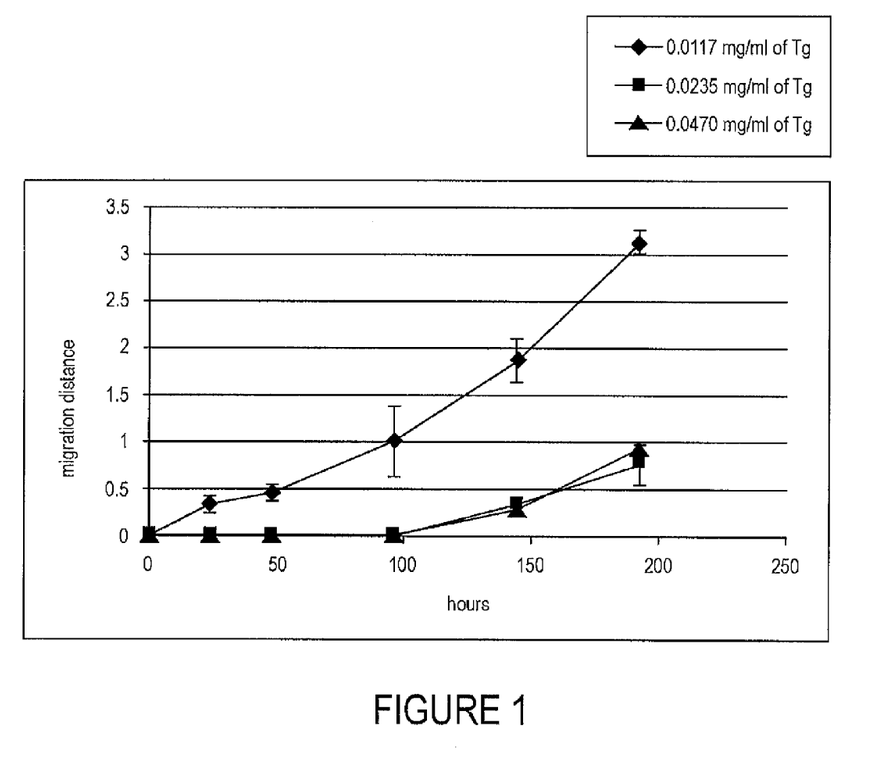
FIG. 1. Migration of the stem cells from the hydrogel with different concentration of tranglutaminase (Tg).
Figure 2:
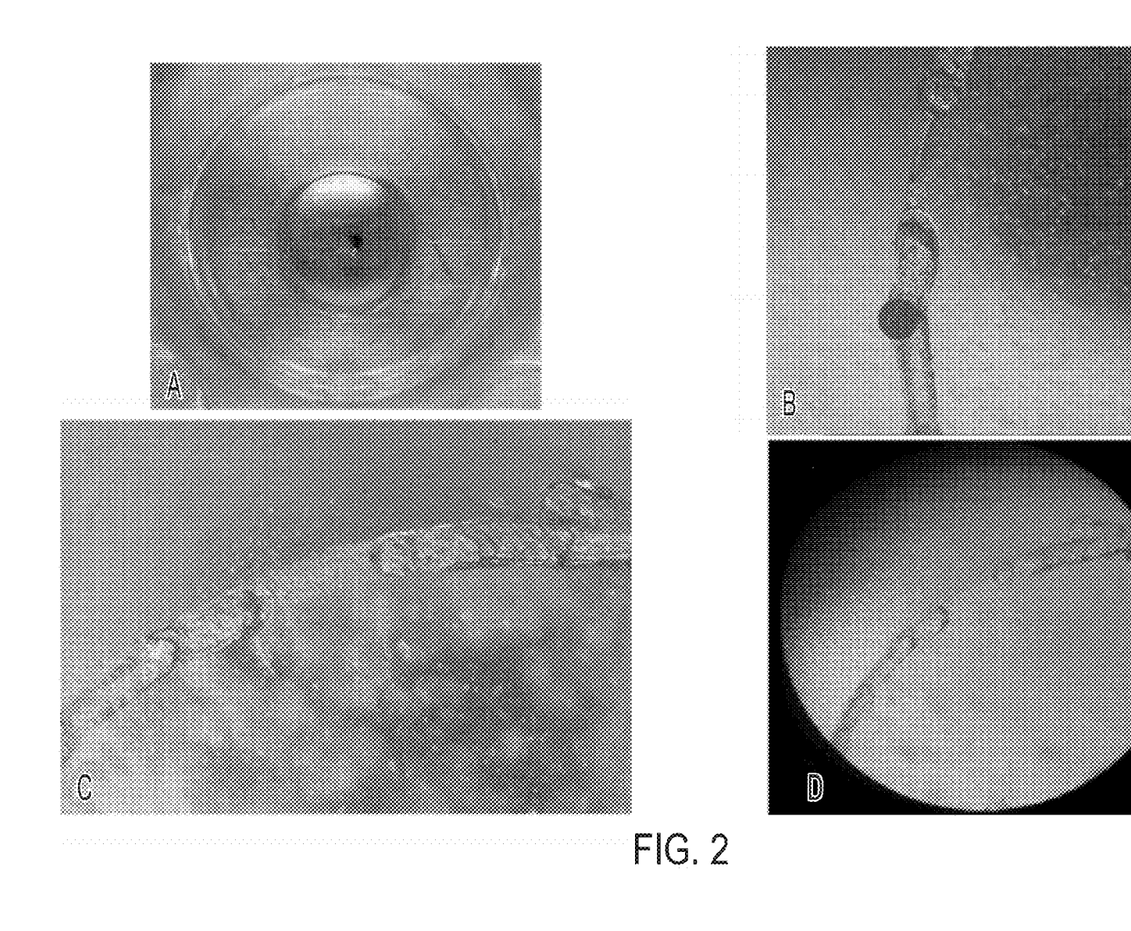
FIG. 2. A. Hydrogel solidified on the middle of the well containing $10^6$/ml cells. The hydrogel absorbed the DMEM media giving the gel a purple color. B,C,D show the migration of the encapsulated cells from a solidified gel after 1, 6, 8 days respectively.

The gel-Tg hydrogels showed that cells were released at different times depending on the concentration of the transglutaminase administered to the gel before mixing. At low concentration, the cells immediately migrated out of the gel. At higher concentration of 2× and 4× the enzyme, the cells remained within in the gel and were released after 96 hours. FIG. 1 shows the distance the cells migrated away from the gel.

Cell Morphology and Viability

Cell viability test with trypan blue showed the cells are viable within the gel after crosslinking. Cells started out round however by day 3, the cells started to aggregate. By day 4 colonies started to form and by day 7, network like structure started to form. The trypan blue staining also gave indication that the colonized cells were still viable as well.

In Vivo Cell Delivery

Figure 12:
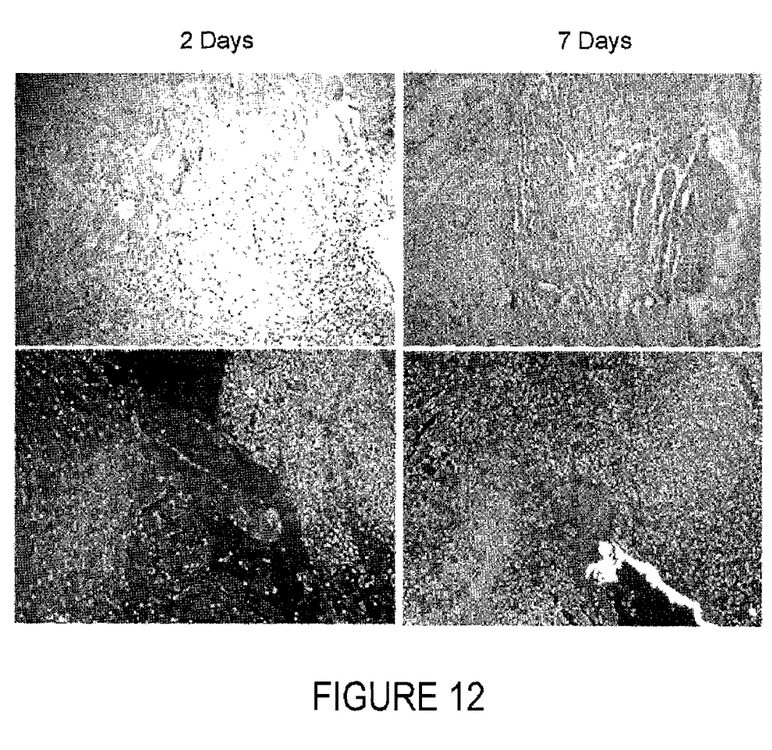
FIG. 12. Histological and fluorescent images of the areas where the GFP MSCs carrying gel-Tg were injected after 2 days and 7 days. Histological slides were stained in H & E. Unstained slides were placed under fluorescent images.

Gel-Tg scaffold is observed to be attached to the surrounding muscle tissue. FIG. 12 shows the gel-Tg as a continuous part of the tissue. From the fluorescence microscope images, the GFP labeled MSC cells are more uniformly spread in the tissue that has gel-Tg incubated for 7 days than 2 days.

Discussion

Cell Viability

Figure 8:
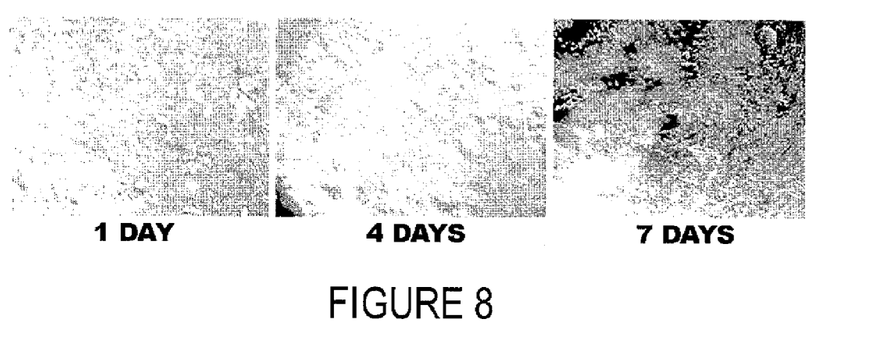
FIG. 8. Cell morphology changes observed with cells encapsulated in the 10% gel-Tg.

Through trypan blue, the stem cells were proven to be viable within the gel. In FIG. 8A, a rounded morphology is observed. Trypan blue also confirmed the colonies to be viable showing transparent cells within the colonies. Some cells in the colonies were perceived to be darker mostly due to an overlapping of other live cells and also due to the occasional dead cells underneath.

10% gelatin was the optimal concentration for proliferation and attachment of the MSC cells. The higher concentration of gelatin increases the number of integrin binding domains and also aids in the rigidity of the gel. 10% gelatin without Tg was observed to gradually dissolve and melt under 37° C. in 10% FBS/DMEM solution. The significant difference observed between transglutaminase treated and non-treated gelatin may be due to the unstable nature of the gelatin at high temperature. 10% gelatin is used for the remainder of the study.

Other Hydrogels and Cell Confinement

Figure 6:
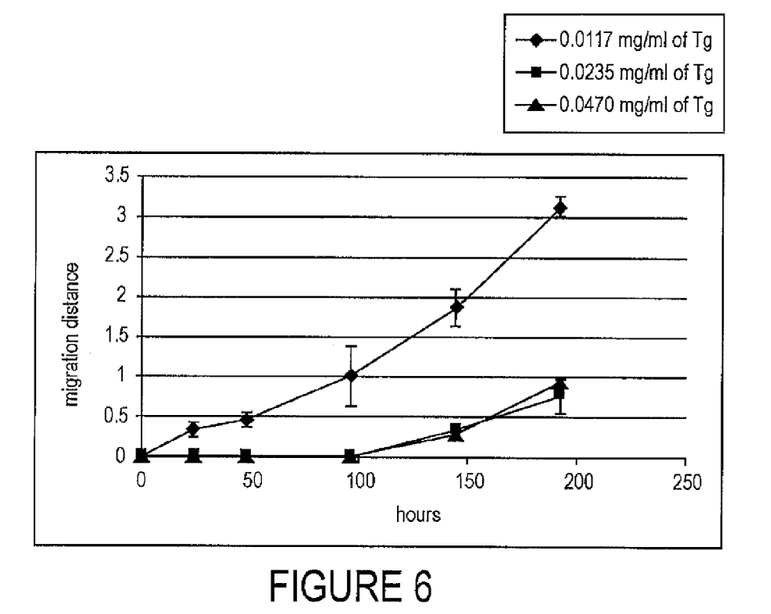
FIG. 6. The distance traveled after the encapsulated MSCs has been released from the gels.
Figure 7:
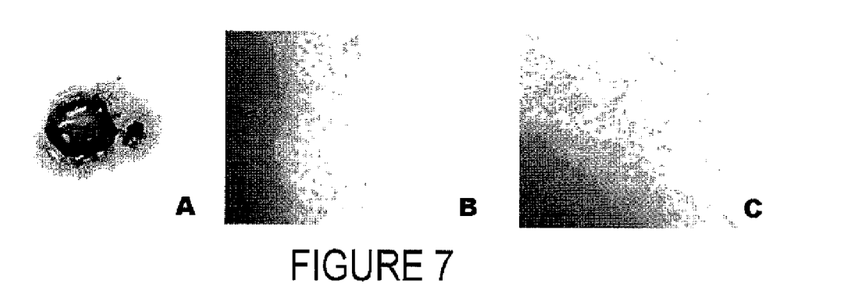
FIG. 7. (A) Intact 10% gelatin gel-Tg gel stained with QuikFix. (B) and (C) show migration at different stages.

A part of our studies solidifies the conclusions based on Yung et al study. The cytotoxicity test concurs with the findings of Yung et al. where it was concluded that transglutaminase mixed with gelatin is noncytotoxic. These studies also show that gelatin crosslinked by microbial transglutaminase will not inhibit proliferation and continue to proliferate once released which is also concluded in Yung et al. However, in this study, a slightly different approach is taken. In Yung, the cells in the hydrogel are released through simulated proteolytic attack by trypsin. But as shown in FIG. 6, the cells can migrate out without the use of trypsin. The general idea was to show the ability to control the release of the cells depending on the amount and concentration of the transglutaminase enzyme. The main focus of this study is to show the gel-Tg is a viable injectable cell delivery device that can polymerize in situ.

Figure 9:
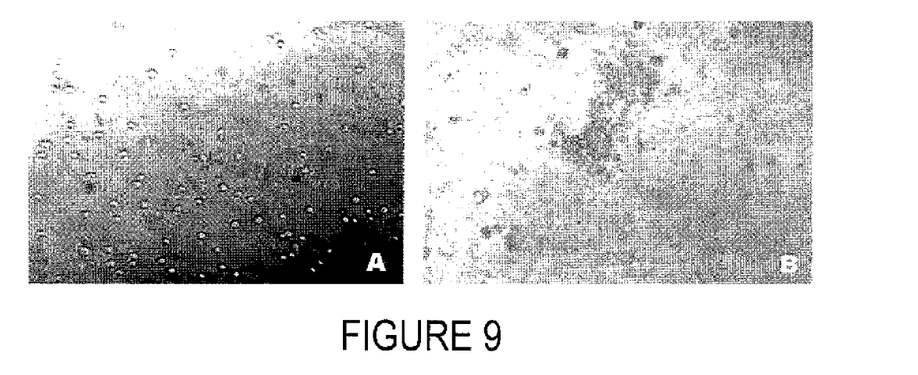
FIG. 9. (A) Trypan blue staining of the gel-Tg at day 1. (B) Trypan blue staining of colonies after 3 days.
Figure 10:
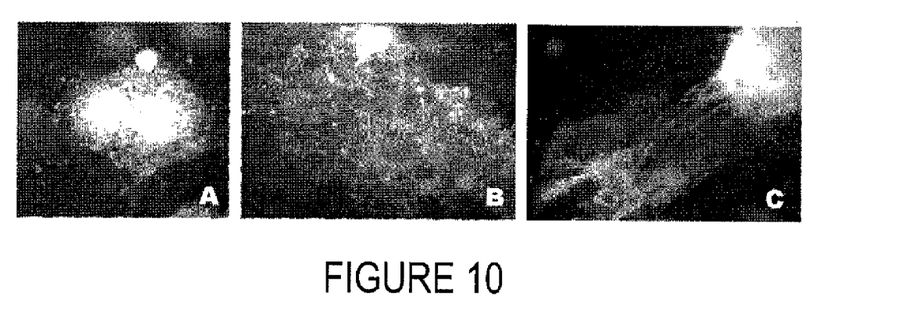
FIG. 10. (A) A fluorescent picture of a cell colony. (B) A colony with a network like morphology. (C) Cellular connection formation between colonies.
Figure 11:
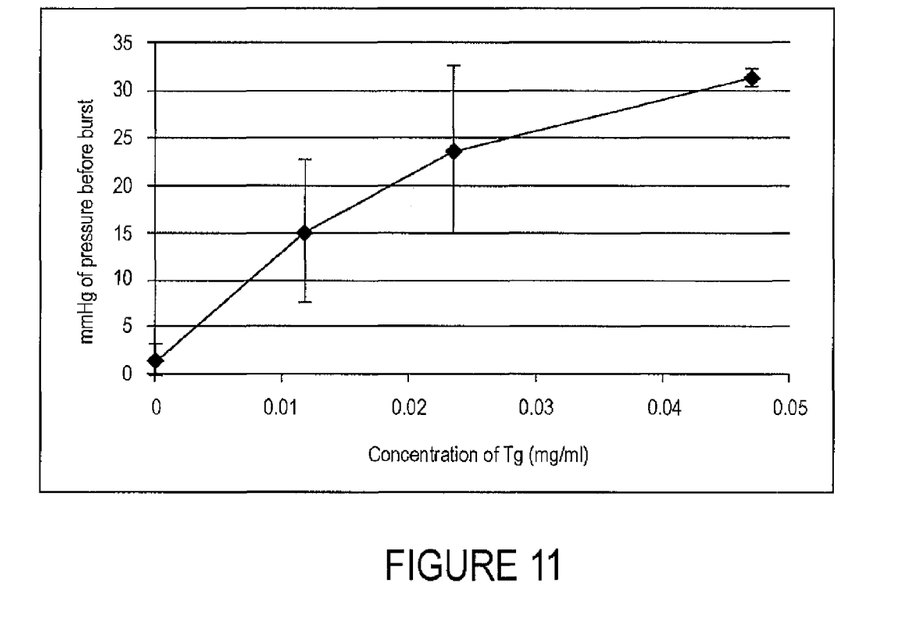
FIG. 11. The resistance to pressure measured in mmHg by gel/Tg with different concentration of Tg.

In our studies, a high concentration of 10% gelatin was used. The high gel concentration helps the gel to become more resistant to proteolytic degradation and should provide better anchorage for integrin to bind. When FIG. 9B is viewed, the encapsulated cells are capable of forming colonies around day 3-4 and later network like mesh around day 7-9. It is well known that cells in living tissue use degradative MMP enzymes to migrate from one location to another. As the amount of transglutaminase increased, the migration became more difficult and it takes more time for the cell to degrade its path and leave the gel. This study shows this confinement can be used as an advantage by controlling the time for releasing the cells.

A constrictive gel may pose a problem in the encapsulation of cells. Hoshikawa et al[26] used a styrenated natural polymer gelatin to encapsulate chondrocytes. The gel combined with the photopolymer crosslinked under visable light. Similar to this study, the hydrogel is able to polymerize in situ after being injected through a needle. However, the polymer seems to have low cell viability due to its tightly crosslinked structure.

Yung et al [10] stated that high concentration of gel may be too confining for most cell types. However in our study, the cells appear to migrate well and survive. A difference can be stated that the previous study uses type A gelatin with a higher bloom. The difference may account for the type A gels to become more constrictive with the crosslinking than a crosslinked gel with type B gelatin. Type B gelatin contains a lower number of glutamine amino acids due to a basic process in which the gelatin is purified. [7] The basic process hydrolyzes the glutamine as well as the asparagines to glutamate and aspartic acid [27]. Type A gelatin is able to retain most of it glutamine due to an acidic process of purification which involves less hydrolysis [27]. The reduction of confinement at higher concentration of gelatin may be possible with Type B. Higher gelatin content can later lead to a higher resistance to the proteolytic degradation.

Implantation of the Gel/Tg

The feasibility of injecting gelatin-TGase hydrogel as a cell delivery vehicle to be used in tissue repair was studied in an animal model. A pilot study was conducted in which GFP labeled MSC in gelatin-TGase was injected into a rotator cuff of drat. Using the gelation time table (Table 2), the gel was injected into the animal by a 23 gauge needle with relative ease. The area of injection was located by the suture marker left at the time of the initial surgery. From the histology, the gel was distinguished by the difference in density and appearance from the surrounding tissue. The histology showed that the gel was able to attach itself onto the surrounding muscle tissue (FIG. 12). The identification of the MSCs was confirmed by fluorescence imaging. In the two-day explant, the cells were found concentrated in the gelatin-TGase. By the 7th day, the explants showed that the MSC spread out uniformly into the surrounding tissue. The gel was also found to be smaller and held fewer cells.

CONCLUSION

The inventors have developed a transglutaminase crosslinked gelatin gel for minimum invasive cell delivery. They have shown that the gel/Tg is a nontoxic, adhesive and biodegradable hydrogel and has the potential to carry cells to a wound site. When homogeneously mixed with cells, gel/cell composite can be locally delivered to the lesion site by injection. The gel/Tg not only maintains the carried cells to be viable and proliferative, but it also serves as a scaffold to support the migration of surrounding cells for tissue repair. The in-situ cross-linking between gelatin chains and endogenous collagen of tissue ECM can create a strong attachment between the matrices and prevent cells from diffusion. This cell delivery system will be useful for rotator cuff tear and intervertebral disc repair.

REFERENCES

2. Atala, A., *Recent developments in tissue engineering and regenerative medicine*. Curr Opin Pediatr, 2006. 18(2): p. 167-71.
3. Mooney, D. J. and H. Vandenburgh, *Cell delivery mechanisms for tissue repair*. Cell Stem Cell, 2008. 2(3): p. 205-13.
4. Okino, H., et al., *In situ hydrogelation of photocurable gelatin and drug release*. J Biomed Mater Res, 2002. 59(2): p. 233-45.
5. Einerson, N. J., K. R. Stevens, and W. J. Kao, *Synthesis and physicochemical analysis of gelatin-based hydrogels for drug carrier matrices*. Biomaterials, 2003. 24(3): p. 509-23.
6. Eastoe, J. E., *The amino acid composition of mammalian collagen and gelatin*. Biochem J, 1955. 61(4): p. 589-600.
7. Veis, A., *The macromolecular chemistry of gelatin*. 1964, New York: Academic Press.
8. Ruoslahti, E., *RGD and other recognition sequences for integrins*. Annu Rev Cell Dev Biol, 1996. 12: p. 697-715.
9. Elliott, J. T., et al., *Thin Films of Collagen Affect Smooth Muscle Cell Morphology*. Langmuir, 2003. 19(5): p. 1506-1514.
10. Yung, C. W., et al., *Transglutaminase crosslinked gelatin as a tissue engineering scaffold*. J Biomed Mater Res A, 2007. 83(4): p. 1039-46.
11. Greenberg, C. S., P. J. Birckbichler, and R. H. Rice, *Transglutaminases: multifunctional cross-linking enzymes that stabilize tissues*. FASEB J, 1991. 5(15): p. 3071-7.
12. Nurminskaya, M. and M. T. Kaartinen, *Transglutaminases in mineralized tissues*. Front Biosci, 2006. 11: p. 1591-606.
13. Isobe, T., et al., *Activity-independent cell adhesion to tissue-type transglutaminase is mediated by alpha4beta1 integrin*. Eur J Cell Biol, 1999. 78(12): p. 876-83.
14. Takahashi, H., et al., *Tissue transglutaminase, coagulation factor XIII, and the pro-polypeptide of von Willebrand factor are all ligands for the integrins alpha 9beta 1 and alpha 4beta 1*. J Biol Chem, 2000. 275(31): p. 23589-95.
15. Sakamoto, H., et al., *ε-(γ-Glutamyl)lysine Crosslink Distribution in Foods as Determined by Improved Method*. Journal of Food Science, 1995. 60(2): p. 416-420.

16. Yokoyama, K., N. Nio, and Y. Kikuchi, *Properties and applications of microbial transglutaminase.* Appl Microbiol Biotechnol, 2004. 64(4): p. 447-54.
17. Folk, J. E., *Mechanism and basis for specificity of transglutaminase-catalyzed epsilon-(gamma-glutamyl) lysine bond formation.* Adv Enzymol Relat Areas Mol Biol, 1983. 54: p. 1-56.
18. Chau, D. Y., et al., *The cellular response to transglutaminase-cross-linked collagen.* Biomaterials, 2005. 26(33): p. 6518-29.
19. Ugural, A. C., *Stresses in plates and shells, 2nd Edition.* 1999, New York: McGraw-Hill.
20. Rice, M. A. and K. S. Anseth, *Controlling cartilaginous matrix evolution in hydrogels with degradation triggered by exogenous addition of an enzyme.* Tissue Eng, 2007. 13(4): p. 683-91.
21. Dadsetan, M., et al., *Characterization of photo-cross-linked oligo[poly(ethylene glycol)fumarate] hydrogels for cartilage tissue engineering.* Biomacromolecules, 2007. 8(5): p. 1702-9.
22. Barbetta, A., et al., *Enzymatic cross-linking versus radical polymerization in the preparation of gelatin PolyHIPEs and their performance as scaffolds in the culture of hepatocytes.* Biomacromolecules, 2006. 7(11): p. 3059-68.
23. Barbetta, A., et al., *Emulsion templated scaffolds that include gelatin and glycosaminoglycans.* Biomacromolecules, 2008. 9(10): p. 2844-56.
24. Almany, L. and D. Seliktar, *Biosynthetic hydrogel scaffolds made from fibrinogen and polyethylene glycol for 3D cell cultures.* Biomaterials, 2005. 26(15): p. 2467-77.
25. Weng, L., et al., *Non-cytotoxic, in situ gelable hydrogels composed of N-carboxyethyl chitosan and oxidized dextran.* Biomaterials, 2008. 29(29): p. 3905-13.
26. Hoshikawa, A., et al., *Encapsulation of chondrocytes in photopolymerizable styrenated gelatin for cartilage tissue engineering.* Tissue Eng, 2006. 12(8): p. 2333-41.
27. Gennadios, A., *Protein-Based Films and Coatings.* 2002: CRC Press.
28. Yoon, J.-H., et al., *Optimization of adhesive strength to plywood of gelatin processed from dorsal skin of yellowfin tuna (Thunnus albacares).* Korean Journal of Chemical Engineering, 2008. 25(1): p. 134-138.
29. Chen, T., et al., *Gelatin-based biomimetic tissue adhesive. Potential for retinal reattachment.* J Biomed Mater Res B Appl Biomater, 2006. 77(2): p. 416-22.
30. Sierra, D. H., et al., *A method to determine shear adhesive strength of fibrin sealants.* J Appl Biomater, 1992. 3(2): p. 147-51.
31. Ishihara, M., et al., *Photocrosslinkable chitosan as a dressing for wound occlusion and accelerator in healing process.* Biomaterials, 2002. 23(3): p. 833-40.
32. Sung, H. W., et al., *Evaluation of gelatin hydrogel crosslinked with various crosslinking agents as bioadhesives: in vitro study.* J Biomed Mater Res, 1999. 46(4): p. 520-30.
33. Hirai, J., et al., *Highly oriented, tubular hybrid vascular tissue for a low pressure circulatory system.* ASAIO J, 1994. 40(3): p. M383-8.

EXAMPLE III

IV Disc and Other Exemplary Applications

IV Disc

The 3D gel/cell matrix may be used alone or in combination with growth factors to facilitate regeneration of the structure of IV disc. Suitable cells for such an injectable cell matrix may be obtained from neucleus pulposus of a mammalian vertebral disc, cartilage, bone marrow, fatty tissues. The crosslinked matrix may be delivered to the IV disc space by injection through a syringe, via a catheter, other method known in the art.

Matrix material was prepared as described above to form a viscous fluid and loaded into a 30 G syringe. Two caudal discs per subject were injected with 10 µL (per disc) of sterile-filtered 0.1% chymopapain in Dulbecco's Modification of Eagle's Growth Medium (DMEM) using an insulin syringe equipped with a 28 gauge needle. In vivo enzyme incubation was allowed to proceed for 72 hours. Subsequently, all discs were flushed repeatedly with Cellgro Complete Medium (without phenol red)+10% FBS+1× antibody/antimycotic solution to provide a secondary substrate for neutralization of any remaining active enzyme and to provide a clear nuclear space. One disc per subject was then injected with 20 µL of a gel mix consisting of pre-fluorescent labeled bone marrow stem cells suspended in flushing medium at a concentration of $2 \times 10^6$ cells/mL. After 2 days, disc were retrieved and under histological process. All specimens were imaged using fluorescence microscope.

Meniscus

Stem cells are considered to repair the meniscus. However the avascular site proved to be challenging for repair for the lack of nutrients. In one study, a scaffold loaded with autologous marrow-derived mesenchymal stem cells that were pre-conditioned in chondrogenic medium were implanted in rabbits with meniscus defects.[1] The study found that cell free scaffold had more fibrous scar tissue than the cell seeded scaffold. Fibrocartilage was higher in content in the cell seeded scaffold. The material used was hyaluronan/gelatin mix. Similarly gelatin transglutaminase can also be used. Mesenchymal stem cells can be pretreated before delivered to the meniscus by injection. Cells after the treatment can be encapsulated by gelatin/Tg gel and delivered to the meniscus area.

Joint Tendon

Tendons are required to have stiffness, strength and also elasticity. However to create scaffolds that have tenocyte like cells, the scaffold usually require some kind of mechanical force applied to the cells to orient them and differentiate them into tenocyte. One study used transfected mesenchymal stem cells that overexpress smad8. [2] Smad8 is a signaling molecule that promotes differentiation of cells into tenocytes. In this case a transfected stem cell can be created and mixed with gel/Tg to be injected through a syringe and administered into a joint. The transfected stem cell can not only differentiate itself but also recruiting endogenous cells into differentiating into tendonlike cells.

In the previous study, cells were implanted with the gels into a damaged rotator cuff. Within seven days the cells were able to diffuse out of the gels with no problems and shown to be localized in the vicinity of the rotator cuff (FIG. 12).

Infarcted Heart

A direct injection of myocytes and skeletal muscle has failed in regenerating tissue on the ventricle wall for an infarcted heart. However mesenchymal stem cells found in bone marrow have shown more promise in repair [3, 4]. The cells seem to replicate, differentiate, and promote myocardial repair. The presence of granulocyte-colony stimulating factor also increases the recruitment of the cells and repair of the heart. [5]. Gelatin/Tg gel can serve as a carrier of the stem cells as well as deploy GCSF from the gel. The gel serves as a scaffold while attaching itself to the infarcted repair site.

Wound Healing

Dermal follicle sheath cells are skin stem cells that aid in the regeneration of dermis after injury. [6] Gelatin/Tg can encapsulate these cells and locally deliver them to the repair site. In many of the double layer scaffold for skin, the gel/Tg can act as the inner layer and also the adhesive layer to the defect site. At the same time, the gel/Tg delivers the dermal follicle sheath cells to aid in repair.

Many modifications and variations of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Angele, P., et al., *Stem cell based tissue engineering for meniscus repair*. J Biomed Mater Res A, 2008. 85(2): p. 445-55.
2. Hoffmann, A., et al., *Neotendon formation induced by manipulation of the Smad8 signalling pathway in mesenchymal stem cells*. J Clin Invest, 2006. 116(4): p. 940-52.
3. Sondergaard, C. S., et al., *Minimal engraftment of human CD34+ cells mobilized from healthy donors in the infarcted heart of athymic nude rats*. Stem Cells Dev, 2008.
4. Orlic, D., et al., *Mobilized bone marrow cells repair the infarcted heart, improving function and survival*. Proc Natl Acad Sci USA, 2001. 98(18): p. 10344-9.
5. Fujita, J., et al., *Administration of granulocyte colony-stimulating factor after myocardial infarction enhances the recruitment of hematopoietic stem cell-derived myofibroblasts and contributes to cardiac repair*. Stem Cells, 2007. 25(11): p. 2750-9.
6. Jahoda, C. A. and A. J. Reynolds, *Hair follicle dermal sheath cells: unsung participants in wound healing*. Lancet, 2001. 358(9291): p. 1445-8.

What is claimed is:

1. A composition capable of being injected through a syringe without clogging for delivering cells to tissue in need of repair, comprising:
   a semi-solid hydrogel comprising cells evenly distributed throughout the hydrogel made by:
   i) mixing transglutaminase and 4-20% gelatin (w/v) for less than an hour such that a semi-solid hydrogel occurs; and
   ii) adding cells to the semi-solid mixture obtained in step i), such that the composition is capable of being injected through a syringe without clogging.

2. The composition according to claim 1, wherein the cells are autologous, embryonic, mesenchymal, or progenitor cells.

3. The composition according to claim 1, wherein the transglutaminase is Ca++ dependent transglutaminase, or C++ independent transglutaminase.

4. The composition according to claim 1, wherein the hydrogel contains peptides that contain glutamine amino acids and/or lysine amino acids.

5. The composition according to claim 1, wherein the tissue in need of repair comprises collagen.

6. The composition according to claim 1, wherein the tissue in need of repair is cartilage, bone, tendon/ligament, meniscus, spinal cord, skin, tendon/ligament of an invertebral disc, or retinal.

7. The composition according to claim 1, wherein the pH of the composition is 7.4.

8. The composition according to claim 1, wherein the gelatin hydrogel comprises 5-10% gelatin (w/v).

9. The composition according to claim 1, wherein the mixture further comprises a buffered saline solution.

10. The composition according to claim 8, wherein said buffered saline solution is a PBS solution.

11. The composition according to claim 10, wherein the ratio of gelatin to buffered saline solution to transglutaminase is 9 to 1 to 0.025 by weight.

12. The composition according to claim 1, further comprising one or more additional bioactive materials selected from the group consisting of fibrinogen, small peptide chains containing RGD, fibronectin, sugar based biopolymers, and glutamine and lysine containing peptides.

* * * * *